(12) United States Patent
Knodel et al.

(10) Patent No.: US 8,066,720 B2
(45) Date of Patent: Nov. 29, 2011

(54) SURGICAL METHOD FOR STAPLING TISSUE

(75) Inventors: Bryan D. Knodel, Flagstaff, AZ (US); Benjamin J. Matthias, San Mateo, CA (US)

(73) Assignee: Cardica, Inc., Redwood City, CA (US)

( * ) Notice: Subject to any disclaimer, the term of this patent is extended or adjusted under 35 U.S.C. 154(b) by 504 days.

(21) Appl. No.: 12/343,048

(22) Filed: Dec. 23, 2008

(65) Prior Publication Data

US 2009/0134198 A1 May 28, 2009

Related U.S. Application Data

(60) Division of application No. 11/686,320, filed on Mar. 14, 2007, now Pat. No. 7,533,790, which is a continuation-in-part of application No. 11/672,858, filed on Feb. 8, 2007, now Pat. No. 7,473,258.

(51) Int. Cl.
*A61B 17/068* (2006.01)

(52) U.S. Cl. ......... 606/139; 227/19; 227/82; 227/176.1; 606/219

(58) Field of Classification Search .................. 227/19, 227/176.1, 175.1, 82, 88; 606/139, 219
See application file for complete search history.

(56) References Cited

U.S. PATENT DOCUMENTS

| | | |
|---|---|---|
| 3,526,228 A | 9/1970 | Lyng |
| 3,958,576 A | 5/1976 | Komiya |
| 4,493,322 A | 1/1985 | Becht |
| 4,664,305 A | 5/1987 | Blake, III et al. |
| 4,667,674 A | 5/1987 | Korthoff et al. |

(Continued)

FOREIGN PATENT DOCUMENTS

EP 0713684 A2 5/1996

(Continued)

OTHER PUBLICATIONS

"VasoStasis (TM) Vascular Closure System 510(k) Notification", (Oct. 22, 2004).

(Continued)

*Primary Examiner* — Scott A. Smith
(74) *Attorney, Agent, or Firm* — Brian A. Schar

(57) ABSTRACT

An exemplary method for surgically stapling tissue may include providing a surgical stapler that includes at least one staple, a pusher configured to hold at least one staple, a splay arm movable relative to the pusher, where that splay arm includes two spaced-apart splay tips, and a driver movable relative to the pusher; splaying at least one staple by plastically deforming the distalmost staple against the splay tips; and after splaying, closing at least one staple by plastically deforming the distalmost staple against the splay tips. Another exemplary method for surgically stapling tissue may include providing a surgical stapler comprising a plurality of staples, a pusher configured to hold the staples, a splay arm movable relative to the pusher, a driver movable relative to the pusher, wherein the pusher, splay arm and driver are initially in a first configuration relative to one another; splaying at least one staple to a splayed state; after splaying, closing at least one splayed staple, after which the pusher, splay arm and driver are in a second configuration relative to one another; and resetting the stapler to the first configuration of the pusher, splay arm and driver; where the splaying and closing each plastically deform at least one staple.

17 Claims, 9 Drawing Sheets

U.S. PATENT DOCUMENTS

| | | |
|---|---|---|
| 4,669,647 A | 6/1987 | Storace |
| 4,791,707 A | 12/1988 | Tucker |
| 4,796,627 A | 1/1989 | Tucker |
| 4,874,122 A | 10/1989 | Froelich et al. |
| 4,899,745 A | 2/1990 | Laboureau et al. |
| 4,983,176 A | 1/1991 | Cushman et al. |
| 5,007,921 A | 4/1991 | Brown |
| 5,026,390 A | 6/1991 | Brown |
| 5,047,047 A | 9/1991 | Yoon |
| 5,049,152 A | 9/1991 | Simon et al. |
| 5,089,009 A | 2/1992 | Green |
| 5,100,041 A | 3/1992 | Storace |
| 5,170,926 A | 12/1992 | Ruckdeschel et al. |
| 5,201,745 A | 4/1993 | Tayot et al. |
| 5,207,692 A | 5/1993 | Kraus et al. |
| 5,236,440 A | 8/1993 | Hlavacek |
| 5,356,064 A | 10/1994 | Green |
| 5,395,381 A | 3/1995 | Green et al. |
| 5,413,584 A | 5/1995 | Schulze |
| 5,425,489 A | 6/1995 | Shichman et al. |
| 5,431,669 A | 7/1995 | Thompson et al. |
| 5,439,468 A | 8/1995 | Schulze et al. |
| 5,464,416 A | 11/1995 | Steckel |
| 5,531,760 A | 7/1996 | Alwafaie |
| 5,544,802 A | 8/1996 | Crainich |
| 5,601,574 A | 2/1997 | Stefanchik et al. |
| 5,607,436 A | 3/1997 | Pratt et al. |
| 5,662,662 A | 9/1997 | Bishop et al. |
| 5,662,681 A | 9/1997 | Nash et al. |
| 5,674,231 A | 10/1997 | Green et al. |
| 5,695,504 A | 12/1997 | Gifford, III et al. |
| 5,715,987 A | 2/1998 | Kelley et al. |
| 5,725,554 A | 3/1998 | Simon et al. |
| 5,782,397 A | 7/1998 | Koukline |
| 5,810,846 A | 9/1998 | Virnich et al. |
| 5,829,662 A | 11/1998 | Allen et al. |
| 5,843,124 A | 12/1998 | Hammerslag |
| 5,910,155 A | 6/1999 | Ratcliff et al. |
| 5,921,997 A | 7/1999 | Fogelberg et al. |
| 6,022,372 A | 2/2000 | Kontos |
| 6,197,042 B1 | 3/2001 | Ginn et al. |
| 6,277,131 B1 | 8/2001 | Kalikow |
| 6,277,140 B2 | 8/2001 | Ginn et al. |
| 6,302,898 B1 | 10/2001 | Edwards et al. |
| 6,322,580 B1 | 11/2001 | Kanner |
| 6,348,064 B1 | 2/2002 | Kanner |
| 6,352,541 B1 | 3/2002 | Kienzle et al. |
| 6,368,341 B1 | 4/2002 | Abrahamson |
| 6,371,974 B1 | 4/2002 | Brenneman et al. |
| 6,391,048 B1 | 5/2002 | Ginn et al. |
| 6,450,390 B2 | 9/2002 | Heck et al. |
| 6,451,031 B1 | 9/2002 | Kontos |
| 6,461,364 B1 | 10/2002 | Ginn et al. |
| 6,494,896 B1 | 12/2002 | D'Alessio et al. |
| 6,506,210 B1 | 1/2003 | Kanner |
| 6,508,828 B1 | 1/2003 | Akerfeldt et al. |
| 6,524,321 B2 | 2/2003 | Kanesaka |
| 6,524,326 B1 | 2/2003 | Zhu et al. |
| 6,533,762 B2 | 3/2003 | Kanner et al. |
| 6,540,735 B1 | 4/2003 | Ashby et al. |
| 6,623,510 B2 | 9/2003 | Belef et al. |
| 6,626,918 B1 | 9/2003 | Ginn et al. |
| 6,632,238 B2 | 10/2003 | Ginn et al. |
| 6,652,539 B2 | 11/2003 | Shipp et al. |
| 6,676,685 B2 | 1/2004 | Pedros et al. |
| 6,695,867 B2 | 2/2004 | Ginn et al. |
| 6,719,777 B2 | 4/2004 | Ginn et al. |
| 6,726,704 B1 | 4/2004 | Loshakove et al. |
| 6,743,248 B2 | 6/2004 | Edwards et al. |
| 6,749,621 B2 | 6/2004 | Pantages et al. |
| 6,755,842 B2 | 6/2004 | Kanner et al. |
| 6,767,356 B2 | 7/2004 | Kanner et al. |
| 6,773,438 B1 | 8/2004 | Knodel et al. |
| 6,780,197 B2 | 8/2004 | Roe et al. |
| 6,942,674 B2 | 9/2005 | Belef et al. |
| 7,056,330 B2 | 6/2006 | Gayton |
| 7,473,258 B2 | 1/2009 | Clauson et al. |
| 7,533,790 B1 * | 5/2009 | Knodel et al. ............. 227/175.1 |
| 2001/0007077 A1 | 7/2001 | Ginn et al. |
| 2001/0021855 A1 | 9/2001 | Levinson |
| 2002/0072768 A1 | 6/2002 | Ginn |
| 2002/0082641 A1 | 6/2002 | Ginn et al. |
| 2002/0133193 A1 | 9/2002 | Ginn et al. |
| 2002/0151921 A1 | 10/2002 | Kanner et al. |
| 2002/0156495 A1 | 10/2002 | Brenneman et al. |
| 2002/0193808 A1 | 12/2002 | Belef et al. |
| 2003/0078598 A1 | 4/2003 | Ginn et al. |
| 2003/0097140 A1 | 5/2003 | Kanner |
| 2003/0100920 A1 | 5/2003 | Akin et al. |
| 2003/0109890 A1 | 6/2003 | Kanner et al. |
| 2003/0158577 A1 | 8/2003 | Ginn et al. |
| 2003/0158578 A1 | 8/2003 | Pantages et al. |
| 2003/0229367 A1 | 12/2003 | Viola |
| 2003/0229368 A1 | 12/2003 | Viola |
| 2004/0002681 A1 | 1/2004 | McGuckin, Jr. et al. |
| 2004/0010285 A1 | 1/2004 | Carley et al. |
| 2004/0059375 A1 | 3/2004 | Ginn et al. |
| 2004/0073236 A1 | 4/2004 | Carley et al. |
| 2004/0073255 A1 | 4/2004 | Ginn et al. |
| 2004/0153122 A1 | 8/2004 | Palermo |
| 2004/0153123 A1 | 8/2004 | Palermo et al. |
| 2004/0176798 A1 | 9/2004 | Epstein et al. |
| 2004/0193189 A1 | 9/2004 | Kortenbach et al. |
| 2004/0225301 A1 | 11/2004 | Roop et al. |
| 2005/0021054 A1 | 1/2005 | Ainsworth et al. |
| 2005/0021062 A1 | 1/2005 | Dennis |
| 2005/0131460 A1 | 6/2005 | Gifford, III et al. |
| 2006/0200197 A1 | 9/2006 | Brenzel et al. |
| 2006/0217744 A1 | 9/2006 | Bender et al. |

FOREIGN PATENT DOCUMENTS

| | | |
|---|---|---|
| KR | 2000-46780 | 7/2000 |
| KR | 1020000046780 | 7/2000 |
| WO | WO-99/62408 | 12/1999 |
| WO | WO-00/07640 | 2/2000 |
| WO | WO-00/56223 | 9/2000 |
| WO | WO-00/56227 | 9/2000 |

OTHER PUBLICATIONS

"Summary of Safety and Effectiveness Data (EVS (TM) Vascular Closure System)", (Nov. 3, 2004).

"The EVS(TM) Vascular Closure System by Angiolink", *Business Briefing: US Cardiology 2004*, (2004).

"Closure and Assisted-Compression Device Update", *Endovascular Today*, (Apr. 2004),22.

"Notification of Transmittal of the International Search Report and Written Opinion of the ISA", PCT/US2008/056328, (Jul. 28, 2008).

"Written Opinion of the International Search Authority", PCT/US2008/056328, (Jul. 28, 2008).

"PCT International Search Report", PCT/US2008/056328, (Jul. 28, 2008).

"EPO Search Report and Opinion", EP 08731757.4, based on PCT/US2008/056328.

* cited by examiner

SURGICAL METHOD FOR STAPLING TISSUE

This application is a divisional of U.S. patent application Ser. No. 11/686,320, filed Mar. 14, 2007, now U.S. Pat. No. 7,533,790, which in turn is a continuation-in-part of U.S. patent application Ser. No. 11/672,858, filed Feb. 8, 2007, now U.S. Pat. No. 7,473,258, all of which are hereby incorporated by reference in their entirety.

FIELD OF THE INVENTION

The present invention relates generally to a surgical stapler and a method for surgical stapling.

BACKGROUND

Traditionally, suture has been utilized to close wounds and incisions, to attach separate tissue structures to one another, and to perform other medical and surgical functions. However, suturing requires skill to perform, particularly suturing procedures that are complex, time-consuming and/or difficult. Further, suturing may be impractical or unfeasible in certain situations. For example, in a minimally-invasive surgical procedure through a small opening (often referred to as an access port) in the patient's body, that port may not be large enough to allow suturing to be performed through it. If the port were enlarged to allow suturing, the benefits of minimally-invasive surgery through a small access port would be reduced or eliminated altogether. Indeed, as surgical technology progresses, the size of the access ports required in the body to perform minimally-invasive surgery decreases. For example, micro-laparoscopy utilizes instruments having a diameter of only 2-3 millimeters to perform procedures such as laparoscopic cholecystectomy and inguinal hernia repair. When instruments of such small diameter are used, the ports in the body through which they are inserted need be only 2-3 millimeters in diameter as well, resulting in minimal or no scarring of the patient after the procedure is completed. However, it is difficult or impossible to perform suturing within the patient's body through ports of such small size.

BRIEF DESCRIPTION OF THE DRAWINGS

The use of the same reference symbols in different figures indicates similar or identical items.

DETAILED DESCRIPTION

Figure 1:
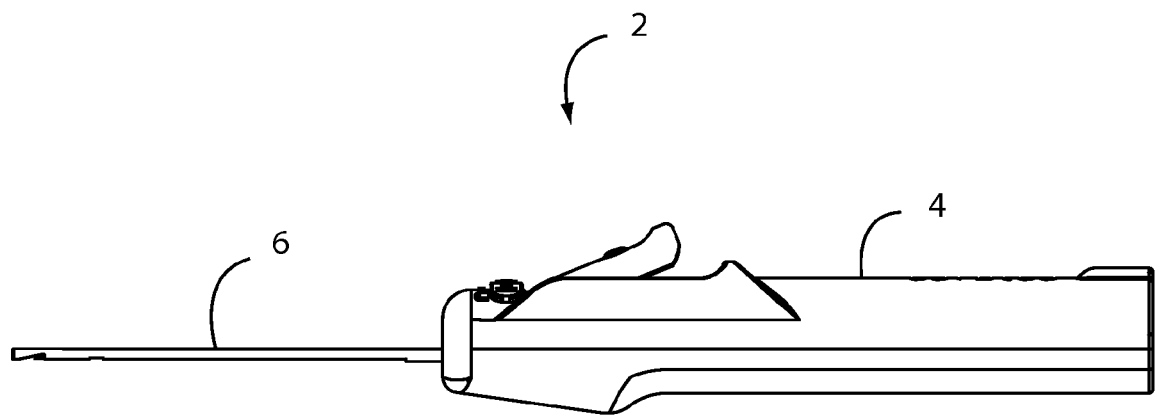
FIG. 1 is a side view of an exemplary surgical stapler.

Referring to FIG. 1, a surgical stapler 2 includes a handle 4 connected to an effector 6. Alternately, the surgical stapler 2 may be configured differently. For example, the effector 6 may be indirectly connected to the handle 4 via an intermediate structure, such as a rigid, articulated or flexible shaft (not shown). The handle 4 may have any suitable configuration, as described in greater detail below. The effector 6 may be sized to pass through an access port in a patient for use in a minimally-invasive surgical procedure. The effector 6 may be sized and shaped to allow it to be inserted through an access port in a patient of 5 mm in diameter or less. Alternately, the effector 6 may be sized and/or shaped differently. The effector 6 may be substantially rigid, substantially flexible, or a combination of both. The handle 4 may include one or more triggers, levers, knobs, buttons or other input features used to actuate and/or control the effector 6.

Figure 2:
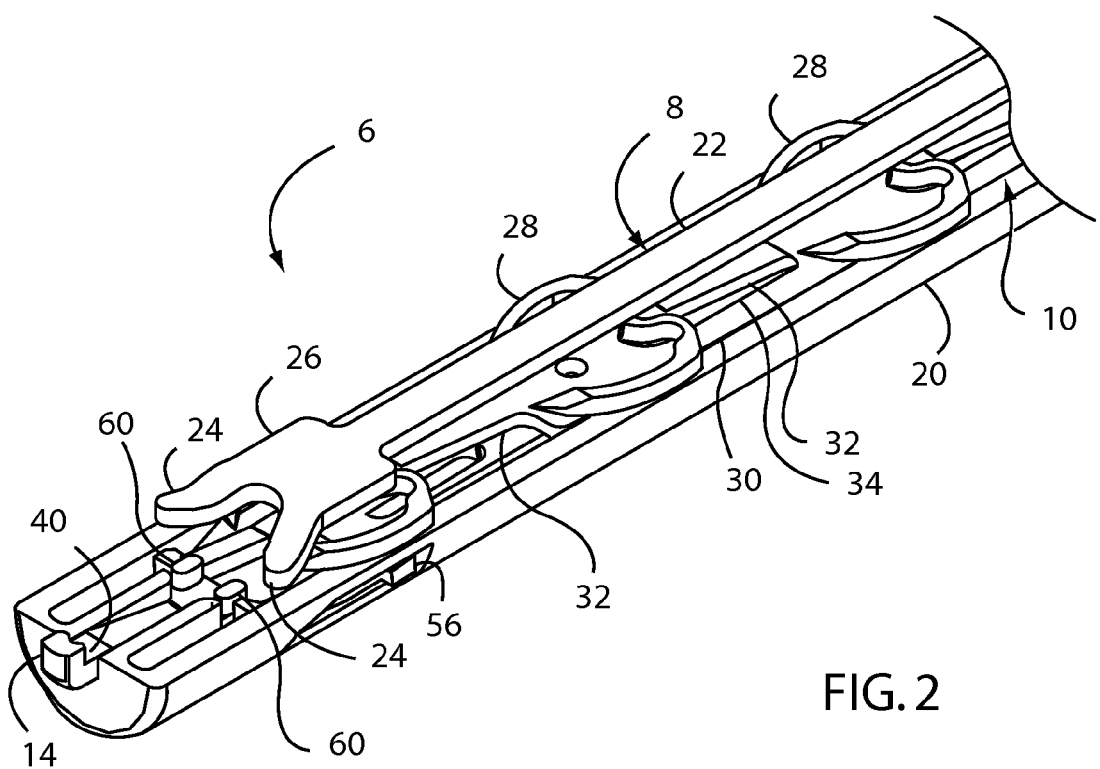
FIG. 2 is a cutaway perspective view from above of an exemplary effector of the surgical stapler of FIG. 1.
Figure 3:
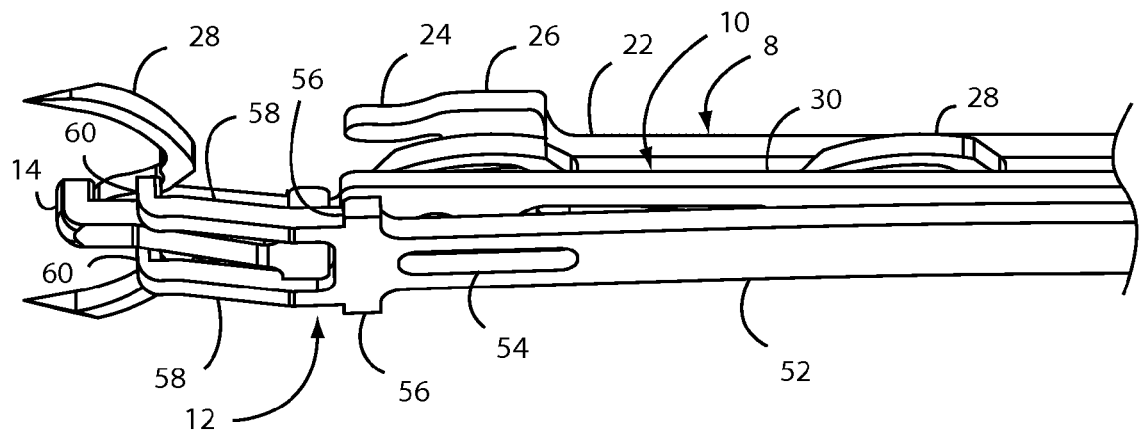
FIG. 3 is a cutaway perspective view from below of an exemplary effector of the surgical stapler of FIG. 1.

Referring to FIGS. 2-3, the effector 6 may include a driver 8, a pusher 10, a splay arm 12, an anvil 14, an anti-backup rack 16, an upper case half 18, and a lower case half 20. The terms "upper," "lower," "upward," "downward," "up," "down," "below," "above" and the like are used solely for convenience in this document; such terms refer to directions on the printed page and do not limit the orientation of the effector 6 in use. The effector 6 may include additional, or fewer, components.

An exemplary driver 8 may be generally elongated in the longitudinal direction, and may be thin. The driver 8 may be stamped from a thin sheet of metal or other material, or may be otherwise fabricated. The driver 8 may include a longitudinally-extending bar 22 located at the proximal end of the driver 8. The driver 8 may be forked or otherwise configured at its distal end. As one example, the driver 8 may include two prongs 24 at its distal end. The proximal end of each prong 24 may be connected to a crossbar 26 that in turn is connected to the bar 22. The crossbar 26 may be substantially perpendicular to the prongs 24 and to the crossbar 26, or may be oriented differently relative to the bar 22. The crossbar 26 may be substantially square. However, the crossbar 26 may be rectangular, oval, cylindrical, or have any other suitable shape. Alternately, the prongs 24 may be connected directly to the bar 22, without the use of the crossbar 26. Alternately, more than two prongs 24, or a single prong 24, may be utilized. Each prong 24 may be shaped in any suitable manner. The distal end of one prong 24 or both prongs 24 may be curved or angled downward. As one example, a distal portion of at least one prong 24 may be below and substantially parallel to the bar 22, where that prong 24 curves upward proximally to that distal portion to connect to the crossbar 26. Alternately, the distal end of at least one prong 24 may be substantially in the same plane as the remainder of the prong 24, or may be curved or angled upward.

Figure 4:
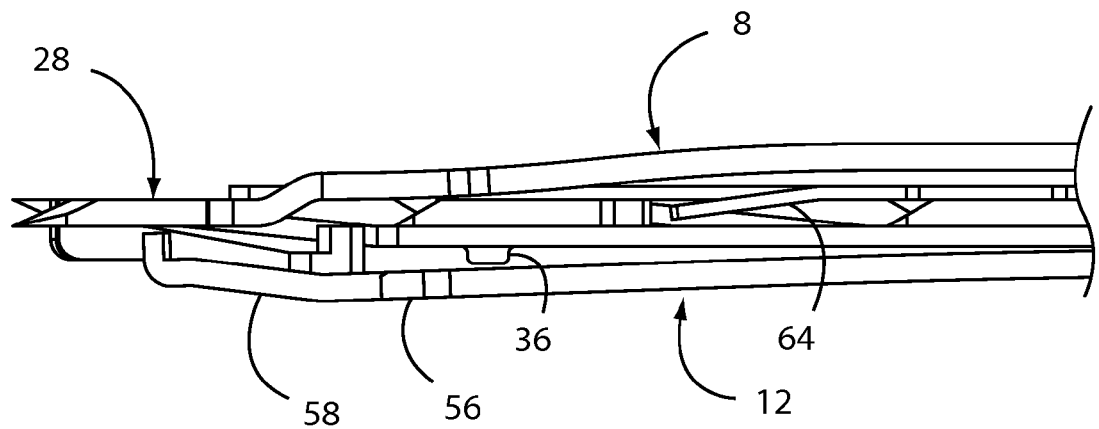
FIG. 4 is a cutaway side view of an exemplary effector of the surgical stapler of FIG. 1.

The pusher 10 may be located directly below the driver 8. Alternately, the pusher 10 may be positioned differently relative to the driver 8. The pusher 10 is oriented relative to the driver 8 such that the longitudinal centerlines of the pusher 10 and driver 8 are substantially parallel. Alternately, the pusher 10 and the driver 8 may be oriented differently relative to one another. The pusher 10 and the crossbar 26 of the driver 8 may each have substantially the same width, but they may have different widths if desired. An exemplary pusher 10 may be generally elongated in the longitudinal direction, and may be thin. The pusher 10 may be stamped from a thin sheet of metal or other material, or may be otherwise fabricated. The pusher 10 holds and advances one or more staples 28. The pusher 10 includes a substantially flat base 30 with one or more tabs 32 extending upward therefrom, such that the distal end of each tab 32 is located above the base 30 and the proximal end of each tab 32 is connected to the base 30. Alternately, the tabs 32 may be configured differently. The tabs 32 are biased upward from the base 30. The base 30 may include one or more apertures 34 defined therein, where a tab 32 extends upward from the proximal end of a corresponding aperture 34. The use of such apertures 34 allows the tabs 32 to be formed by cutting the base 30, such as by laser cutting, resulting in an aperture 34 around and under a corresponding tab 32. However, the apertures 34 need not be present in the base 30, and the pusher 10 may be fabricated in any suitable manner. Referring also to FIG. 4, a camming bump 36 extends downward from the pusher 10 near the distal end of the pusher 10. The function of the camming bump 36 is described in greater detail below. The camming bump 36 may be shaped, sized and fabricated in any suitable manner. As one example, the camming bump 36 may be created by dimpling the pusher 10.

The anvil 14 may be fixed to the pusher 10. Advantageously, the anvil 14 is integral with the pusher 10, and extends from the distal end of the pusher 10. Alternately, the anvil 14 may be connected to the pusher 10 in a different way, or may be connected to a different part of the effector 6. The proximal end of the anvil 14 may be located at the distal end of the pusher 10, or at a different location on the pusher 10. The anvil 14 may curve or angle upward from the distal end of the pusher 10. Alternately, the anvil 14 may be substantially in the same plane as the pusher 10. Advantageously, the distal end of the anvil 14 is substantially blunt. The anvil 14 may include a notch 40 defined in its upper and lateral surfaces, where the notch 40 is oriented upward and is substantially as deep as the thickness of the staple or staples 28. Alternately, the notch 40 may be deeper or shallower, or may be defined in a different surface or surfaces of the anvil 14 or oriented differently. The notch 40 is substantially as long in the longitudinal direction as the corresponding dimension of the staple 28, such that the notch 40 holds the staple 28 securely. Alternately, the notch 40 may be dimensioned differently. The notch 40 holds a staple 28 both as it is being splayed and closed, as described in greater detail below.

Figure 5:
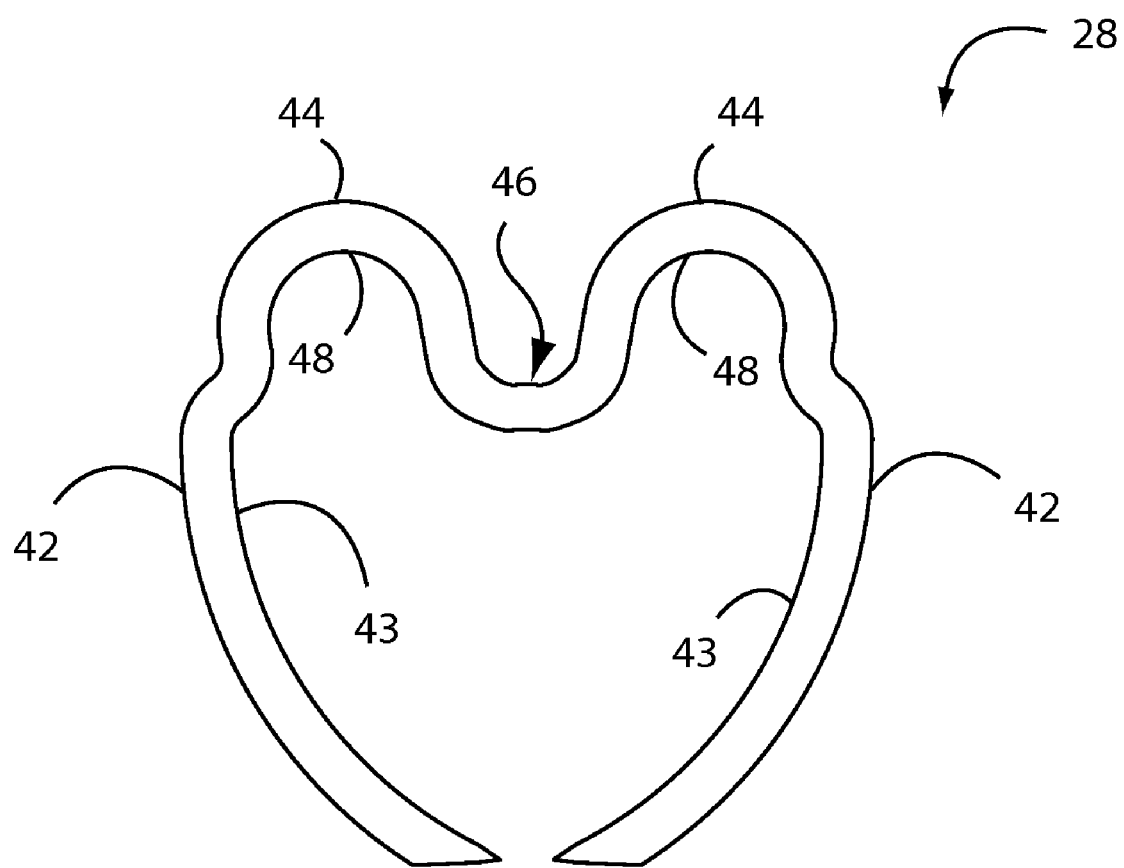
FIG. 5 is a top view of an exemplary staple deployed by the surgical stapler of FIG. 1.
Figure 6:
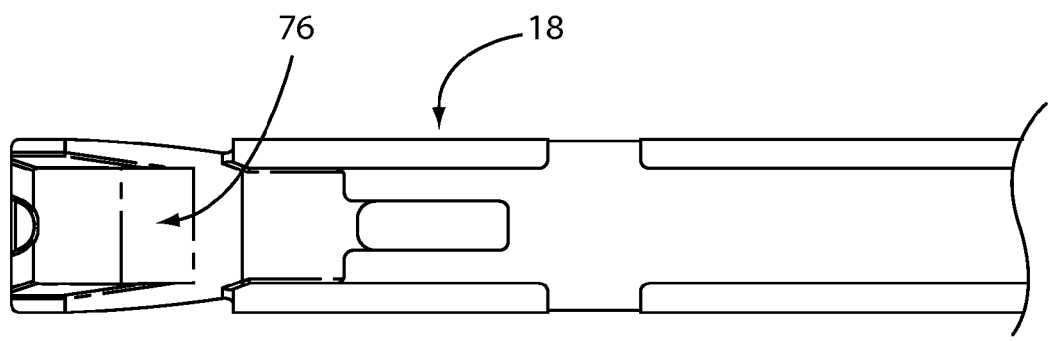
FIG. 6 is a bottom view of an exemplary upper case half of the surgical stapler of FIG. 1.

Referring also to FIG. 5, a staple 28 is positioned distal to each tab 32 of the pusher 10, and may be in contact with the corresponding tab 32. At least one staple 28 may be configured substantially as described in U.S. patent application Ser. No. 11/093,003, filed on Mar. 28, 2005, which is hereby incorporated by reference in its entirety. Alternately, at least one staple 28 may be sized and shaped in any different and suitable manner. As one example, the staple 28 may have a curved M- or W-shape. However, the staple 28 may have any other suitable shape. The staple 28 may have two tines 42, each extending at least partially in the distal direction. The tines 42 may be curved, and may each have a shape and radius of curvature such that the tines 42 are generally not parallel to one another. The radius of curvature may be substantially coincident with the path of travel of the tines 42 during closure of the staple 28. Each tine 42 has an inner surface 43. The staple 28 may be substantially bilaterally symmetrical, although it may be asymmetrical if desired. The staple 28 may be a substantially continuous solid. As used in this document, the term "solid" means that a structure has no slots, holes, apertures or other enclosed or bounded openings defined therein. However, the staple 28 need not be a substantially continuous solid.

The distal end of each tine 42 may have a substantially pointed or sharpened distal end. However, the distal ends of the tines 42 need not be pointed or sharpened, particularly if the cross-sectional area of each tine 42 is small. Advantageously, each tine 42 has a single distal end that is not bifurcated or otherwise forked or split. However, the distal end of at least one tine 42 may be bifurcated, forked, split or otherwise configured. The body of the staple 28 extends proximally from the distal end of one tine 42 and curves or angles relative to the longitudinal centerline of the staple 28. This curve may extend outward from the longitudinal centerline of the staple 28, then toward the longitudinal centerline of the staple 28. Alternately, the tine 42 may curve differently. The body of the staple 28 reaches a peak 44, then extends distally and toward the longitudinal centerline of the staple 28. The body of the staple 28 then reaches a trough 46, then extends proximally and away from the longitudinal centerline of the staple to a second peak 44. The body of the staple 28 continues distally to form the second tine 42, which curves or angles relative to the longitudinal centerline of the staple 28. This curve may extend outward from the longitudinal centerline of the staple 28, then toward the longitudinal centerline of the staple 28. The staple 28 ends at the distal end of the second tine 42. Alternately, the staple 28 may be shaped differently. For example, the staple 28 may have more than two tines 42. A valley 48 is the area on the staple 28 on the other side of the staple 28 from a peak 44. For example, where a peak 44 of the staple 28 includes a convex curve oriented proximally, the corresponding valley 48 is a concave curve opening distally. Advantageously, the staple 28 is substantially solid.

The staple 28 may lie substantially in a single plane. That is, the staple 28 is shaped such that a single plane extends through and substantially bisects the entire staple 28. Alternately, the staple 28 does not lie substantially in a single plane. The longitudinal and lateral dimensions of the staple 28 overall may both be substantially larger than the height of the staple 28. Alternately, the staple 28 may be sized differently.

Advantageously, the staple 28 may be plastically deformable. That is, the staple 28 may undergo a permanent deformation when subjected to a stress exceeding its yield value. In other words, plastic deformation is deformation that remains after the load that caused it is removed, or that would remain if the load were removed. If so, the staple 28 may be fabricated from stainless steel, titanium or any other suitable plastically-deformable material. Alternately, the staple 28 may be elastically deformable. If so, the staple 28 may be fabricated from nickel-titanium alloy or any other suitable elastic or superelastic material. The staple 28 may be fabricated from a single wire or other piece of material, having a rectangular, circular or other cross-section. However, the staple 28 may be fabricated in any suitable manner. The cross-section of the staple 28 may be substantially constant along the entire staple 28, or may vary at different locations along the staple 28. For example, the cross-sectional area of the staple 28 at certain locations may be less than at other locations, in order to promote bending in those locations having a lesser cross-sectional area. The cross-sectional shape of the staple 28 may be square, rectangular, circular, oval or any other suitable shape, and may be substantially constant along the entire staple 28 or vary at different locations along the staple 28.

Referring back to FIGS. 2-3, the splay arm 12 of the effector 6 may be located directly below the pusher 10. Alternately, the splay arm 12 may be positioned differently relative to the pusher 10. The splay arm 12 is oriented relative to the pusher 10 such that the longitudinal centerlines of the splay arm 12 and pusher 10 are substantially parallel. Alternately, the splay arm 12 and pusher 10 may be oriented differently relative to one another. The splay arm 12 may be generally elongated in the longitudinal direction, and may be thin. The splay arm 12 may be stamped from a thin sheet of metal or other material, or may be otherwise fabricated. The splay arm 12 may include a longitudinally-extending bar 52 located at the proximal end of the splay arm 12. An aperture 54 may be defined in the splay arm 12 at or near the distal end of the bar 52, or at a different location on the splay arm 12. The aperture 54 may extend completely through the splay arm 12, or may simply be a recessed area in the upper surface of the splay arm 12. Alternately, the aperture 54 may be omitted. One or more ears 56 may extend laterally from the splay arm 12, each at a longitudinal location on the splay arm 12 substantially even with the distal end of the aperture 54. Alternately, the ears 56 may be located at a different location on the splay arm 12. The splay arm 12 may be forked or otherwise configured at its distal end. As one example, the splay arm 12 may include two splay fingers 58 at its distal end. Each splay finger 58 may extend distally from a location on the splay arm 12 distal to the ears 56 and the aperture 54. Alternately, at least one splay finger 58 extends in a different direction and/or from a different part of the splay arm 12. Alternately, more than two splay fingers 58, or a single splay finger 58, may be utilized. Each splay finger 58 may be shaped in any suitable manner. The distal end of one splay finger 58 or both splay fingers 58 may include a splay tip 60 that is oriented substantially vertically or in any other suitable direction. Each splay tip 60 is positioned such that it can splay a staple 28, as described in greater detail below. The portion of the splay finger 58 between the splay tip 60 and the remainder of the splay arm 12 may be shaped and oriented in any suitable manner. At least one splay finger 58 may be curved or angled upward in the distal direction. Alternately, at least one splay finger 58 may lie in substantially the same plane as a remainder of the splay arm 12. The splay arm 12 may be biased proximally. Such biasing may be performed in any suitable manner, with any suitable structure or mechanism, such as a coil spring, compression spring or tension spring.

Figure 2A:
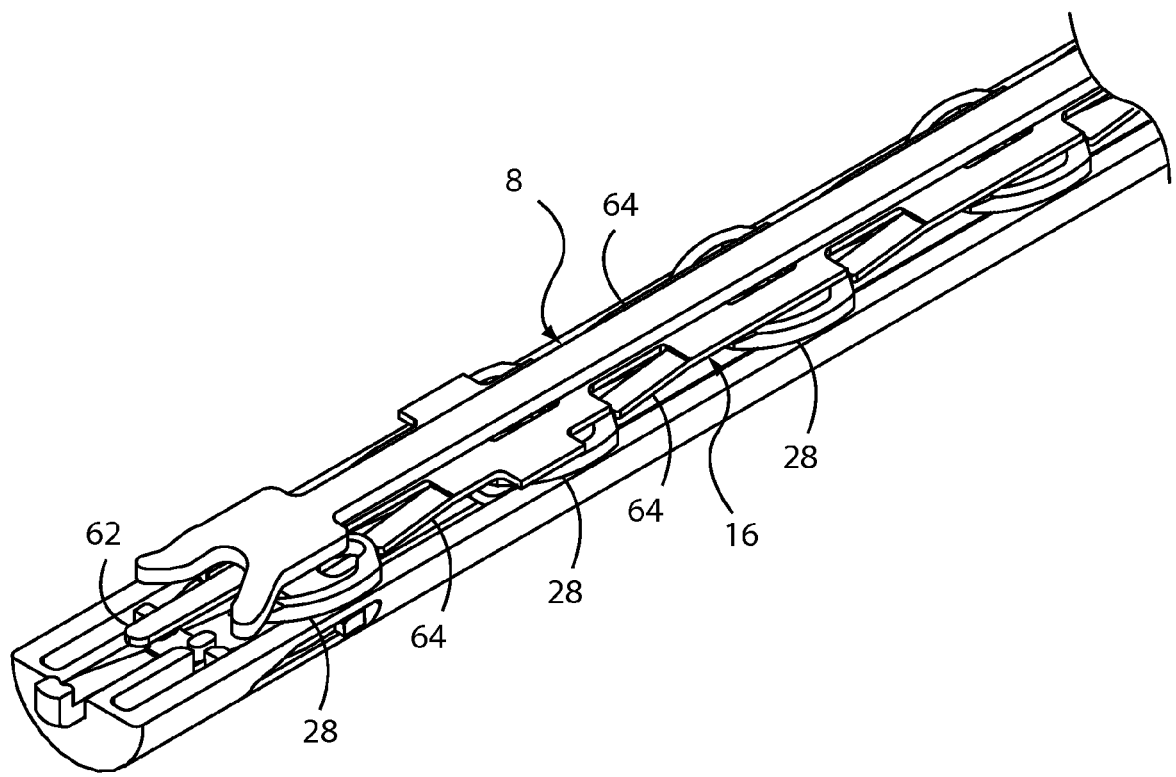
FIG. 2A is the cutaway perspective view of FIG. 2, including an anti-backup rack.

Referring to FIG. 2A, an anti-backup rack 16 may be positioned below the driver 8. Alternately, the anti-backup rack 16 may be positioned differently relative to the driver 8. The anti-backup rack 16 is oriented relative to the driver 8 such that the longitudinal centerlines of the anti-backup rack 16 and driver 8 are generally parallel. Alternately, the anti-backup rack 16 and driver 8 may be oriented differently relative to one another. The anti-backup rack 16 may be generally elongated in the longitudinal direction. The anti-backup rack 16 may be stamped from a thin sheet of metal or other material, or may be otherwise fabricated. The anti-backup rack 16 may include a spine 62 that is oriented substantially longitudinally, and one or more tines 64 extending from the spine 62. Each tine 64 extends in a downward and distal direction. Alternately, at least one tine 64 is oriented differently. Advantageously, at least one pair of tines 64 extends from the spine 62, where each tine 64 in a pair extends from substantially the same longitudinal position along the spine 62. The distal end of each tine 64 is positioned substantially proximal to a corresponding staple 28, such that contact between the staple 28 and the distal end of at least one tine 64 prevents the staple 28 from backing up, as described in greater detail below. Advantageously, each tine 64 of a pair contacts a different peak 44 of the staple 28.

Figure 7:
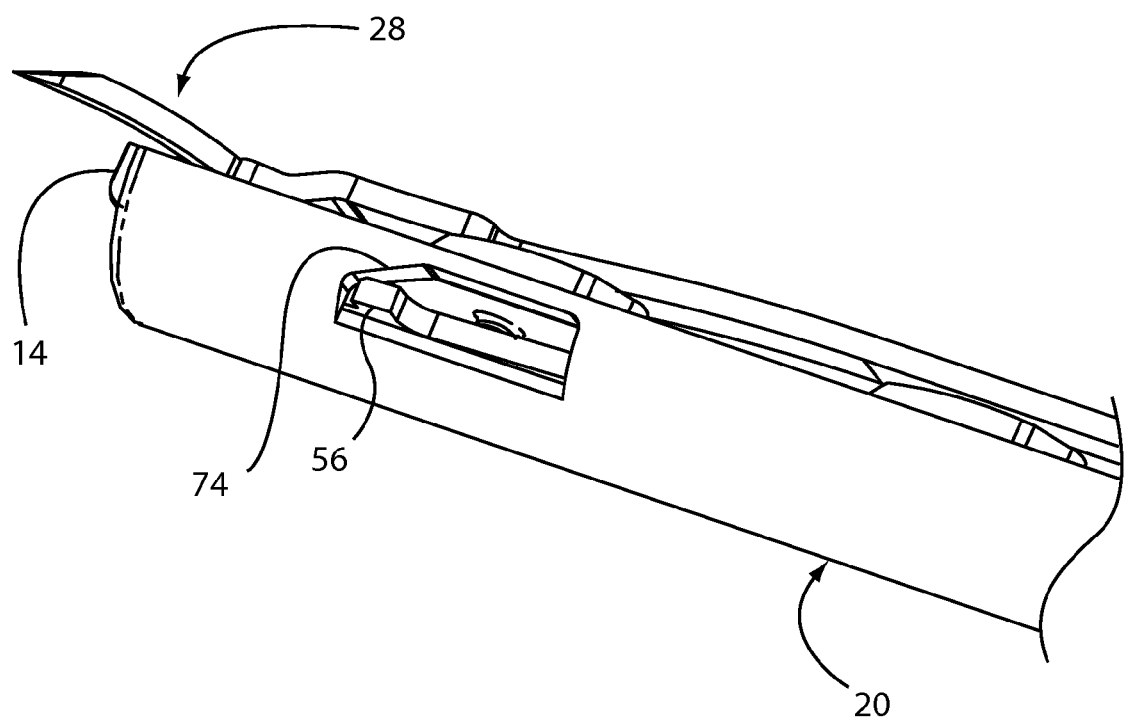
FIG. 7 is a perspective view of the distal end of an exemplary effector of the surgical stapler of FIG. 1, without the upper case half, showing an exemplary lower case half.

Referring to FIGS. 2-4 and 6, the upper case half 18 may be shaped in any suitable manner and fabricated from any suitable material. A ramp 76 may be defined in the inner surface of the upper case half 18, where that ramp is angled or curved downward in the distal direction. Alternately, the ramp 76 need not be defined in the upper case half 18, but may be a component that is connected to the upper case half 18 or other part of the effector 6. Referring also to FIG. 7, the lower case half 20 may be shaped in any suitable manner and fabricated from any suitable material. At least one ramp 74 may be defined in the lower case half 20, where that ramp is angled or curved downward in the distal direction. The ramp 74 may be defined all the way through the lower case half 20, or may be defined into the lower case half 20 without creating an opening in the lower case half 20. Advantageously, two ramps 74 are defined in the lower case half 20, one ramp 74 corresponding to each ear 56 of the splay arm 12. Alternately, the ramp 74 need not be defined in the lower case half 20, but may be a component that is connected to the lower case half 20 or other part of the effector 6. The upper case half 18 may be attached to the lower case half 20 in any suitable manner. The case halves 18, 20 may be referred to collectively as the housing of the stapler 2. Advantageously, the housing is 5 millimeters in diameter or less. Alternately, the housing may have a larger diameter. Alternately, the case halves 18, 20 are each connected to the handle 4 but not to each other.

Integrated Splay Arm and Anvil

Figure 12:
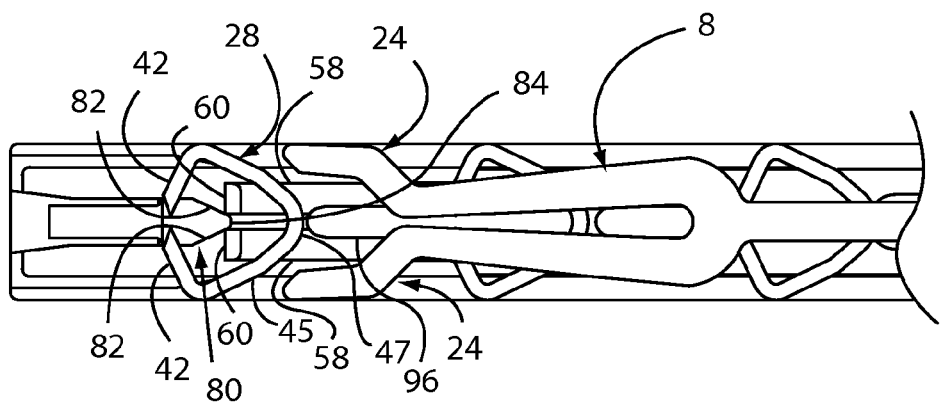
FIG. 12 is a top cutaway view of another exemplary effector of a surgical stapler in an initial configuration.

In another example of an effector 6, the anvil and splay arm may be integrated. For clarity and brevity, only the significant differences between this exemplary effector 6 and the effector 6 described earlier in this document are set forth here. Referring to FIG. 12, the splay arm 12 may include two splay fingers 58 at its distal end. Alternately, more than two splay fingers 58, or a single splay finger 58, may be utilized. Each splay finger 58 may be shaped in any suitable manner. The distal end of one splay finger 58 or both splay fingers 58 may include a splay tip 60 that is oriented substantially vertically or in any other suitable direction. Each splay tip 60 is positioned such that it can splay a staple 28, as described in greater detail below. The portion of the splay finger 58 between the splay tip 60 and the remainder of the splay arm 12 may be shaped and oriented in any suitable manner. At least one splay finger 58 may be curved or angled upward in the distal direction. Alternately, at least one splay finger 58 may lie in substantially the same plane as a remainder of the splay arm 12. The splay fingers 58 are biased toward one another, and are free to move apart from one another upon application of force thereto, as described in greater detail below. The ears of the splay arm 12 described earlier in this document may be omitted from the exemplary splay arm 12 of FIG. 12. Alternately, the splay arm 12 of FIG. 12 may include such ears.

A wedge 80 is defined in or connected to the interior of the lower case half 20. The wedge 80 includes two wedge surfaces 82 that intersect at a wedge apex 84. The wedge surfaces 82 may be substantially planar walls that extend generally upward from the interior of the lower case half 20. Alternately, the wedge surfaces 82 may be shaped, and/or oriented relative to the lower case half 20, in any other suitable manner. The wedge 80 is oriented such that the wedge apex 84 is proximal to the wedge surfaces 82. The wedge apex 84 may be curved, rounded, angular, or have any other suitable shape. When the effector 6 is in the initial state, the splay fingers 58 are positioned such that the wedge apex 84 is located between those splay fingers 58. The splay fingers 58 may be biased to a degree such that contact between the wedge surfaces 82 and the splay fingers 58 holds the splay fingers 58 apart. That is, the splay fingers 58 may apply a compressive force to the wedge surfaces 82. Alternately, the splay fingers 58 are not biased to such a degree that the wedge 80 holds them apart, and the splay fingers 58 do not substantially apply a compressive force to the wedge surfaces 82.

Figure 9:
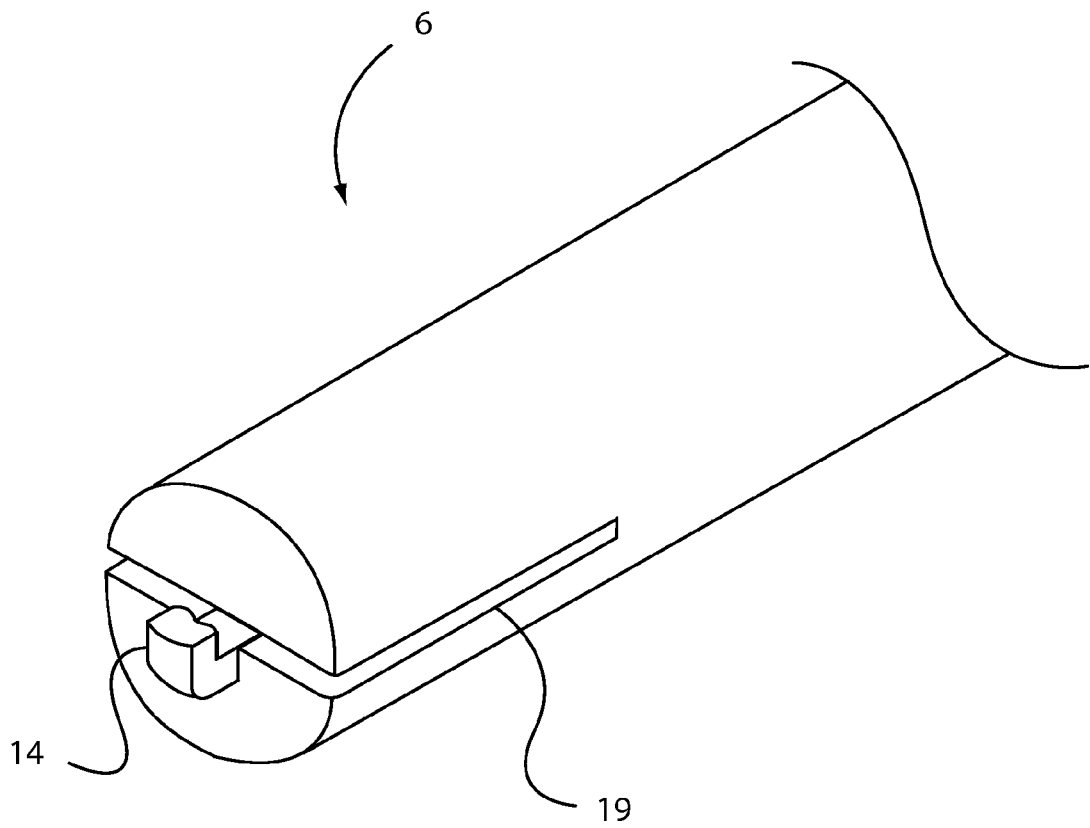
FIG. 9 is a perspective view of the distal end of an exemplary effector of the surgical stapler of FIG. 1.

The driver 8 may be forked or otherwise configured at its distal end. As one example, the driver 8 may include two prongs 24 at its distal end. Each prong 24 may be shaped in any suitable manner. As one example, referring to FIGS. 12 and 15, each prong 24 may include a distal segment 90 connected to a proximal segment 92. The distal segment 90 may be positioned distal to, and laterally outward from, the corresponding proximal segment 92; the distal segment 90 may also be substantially parallel to the proximal segment 92. Additionally, the distal end of one prong 24 or both prongs 24 may be curved or angled downward, as described above. The prongs 24 are biased away from one another, and are free to move apart from one another upon removal of a constraining force applied thereto, as described in greater detail below. The interior of one or both of the case halves 18, 20 may constrain the prongs 24 when the effector 6 is in the initial state. In this way, the overall diameter of the effector 6 is minimized. Referring also to FIG. 9, the prongs 24 may move outward from the case halves 18, 20 through slots 19 in the case halves 18, 20, or through different slots 19 in the case halves 18, 20, as the driver 8 moves distally, as described in greater detail below.

The anvil 14 described above with regard to another exemplary effector 6 is omitted from this exemplary effector 6. The splay tips 60 act as an anvil, as described in greater detail below.

Figure 13:
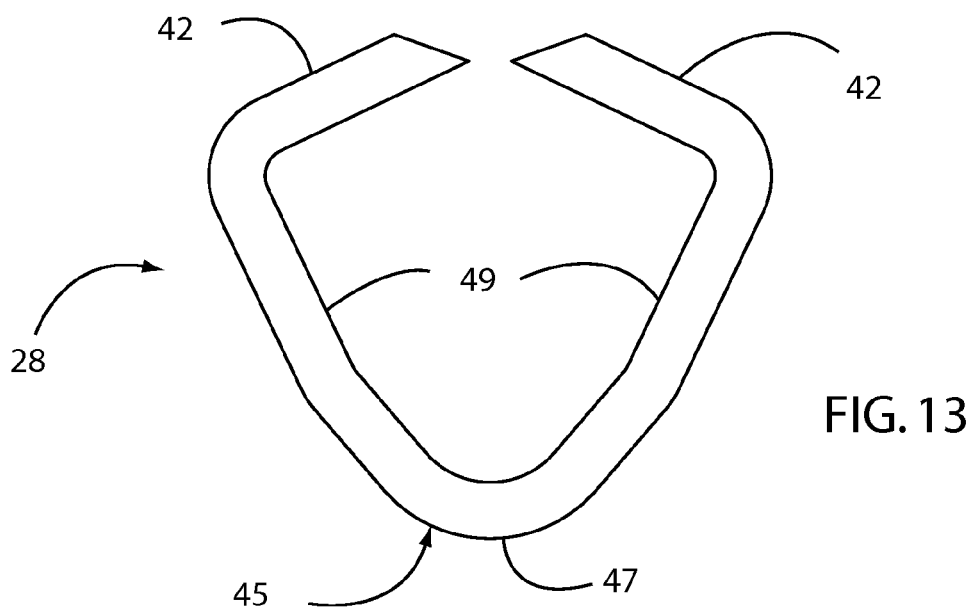
FIG. 13 is a top view of a surgical staple usable with the effector of FIG. 12.

Referring to FIGS. 12-13, at least one staple 28 may initially be in a generally triangular configuration, with the free ends of the tines 42 spaced apart from and generally pointing toward one another. Each tine 42 extends from the distal end of a generally V-shaped spine 45 of the staple 28, with the apex 47 of the spine 45 oriented generally proximally. That is, the staple 28 is composed of a spine 45 and two tines 42 connected to that spine 45. The spine 45 may include two inflection points 49, each on a different side of the spine 45, and laterally spaced away from the apex 47 of the spine 45. At an inflection point 49, the spine 45 is angled or curved. That is, the spine 45 is angled inward toward the longitudinal centerline of the spine 45 distal to an inflection point 49. Alternately, the inflection point 49 may be omitted, if desired. The staple 28 may be deformed such that the spine 45, and not the tines 42, are deformed during splaying and/or closing. However, the tines 42 may be deformed during splaying and/or closing, if desired. The staple 28 of FIG. 12 omits the peaks 44 and trough 46 described with regard to the staple 28 set forth previously in this document. However, the staple 28 may include those features, if desired. The staple 28 may be configured differently, if desired. For example, the staple 28 may be more generally quadrilateral than generally triangular in its initial configuration. As another example, the free ends of the tines 42 initially may be oriented in a different manner relative to one another. As another example, more than two tines 42 may be connected to the spine 45. As another example, the spine 45 may be generally U-shaped or otherwise may be shaped differently.

Handle

The handle 4 may include any mechanism, mechanisms, structure or structures configured to actuate the effector 6. As described later in this document, the handle 4 may be configured to control the motion of the driver 8 and pusher 10, and/or other components of the effector 6. The handle 4 may provide this control in any suitable manner. As one example, a cable extending from the handle 4 may be connected to the driver 8, and another cable extending from the handle 4 may be connected to the pusher 10. As another example, a rod or other substantially rigid structure extending from the handle 4 may be connected to the driver 8, and another rod or other substantially rigid structure extending from the handle 4 may be connected to the pusher 10. As another example, the driver 8 and the pusher 10 may be pneumatically coupled, or otherwise coupled, to the handle 4. As another example, the proximal end of the driver 8 and/or the pusher 10 may extend proximally to the handle 4 and couple directly to the handle 4. Alternately, the driver 8 and pusher 10 may be controllable in a different manner, or may be passive components. The driver 8, pusher 10 and/or other components of the effector 6 may be biased proximally or distally as well, or not biased at all.

The handle 4 may include any suitable mechanism or mechanisms that provide for control of the driver 8 and pusher 10, and may include a source of stored energy for actuating the end effector 4. The source of stored energy may be mechanical (such as a spring), electrical (such as a battery), pneumatic (such as a cylinder of pressurized gas) or any other suitable source of stored energy. The source of stored energy, its regulation, and its use in actuating an effector 6 may be as described in U.S. patent application Ser. No. 10/392,336, filed on Mar. 19, 2003, or U.S. patent application Ser. No. 11/054,265, filed on Feb. 9, 2005, which are herein incorporated by reference in their entirety. The handle 8 may instead, or also, include a connector or connectors suitable for receiving stored energy from an external source, such as a hose connected to a hospital utility source of pressurized gas or of vacuum, or an electrical cord connectable to a power source.

Optionally, the effector 6 may include a cutaway, trough, lumen, ring or other feature (not shown) to allow the effector 6 to follow a guidewire to a treatment site. If so, the surgical stapler 2 may include a flexible shaft (not shown) that connects the handle 4 to the effector 6, such that the handle 4 transmits control input and/or force to the effector 6 via that flexible shaft.

Operation—Staple Deployment

The operation of the surgical stapler 2 is described with regard to a generic surgical procedure. The surgical stapler 2 may be used in the course of any suitable surgical procedure, whether that surgical procedure is minimally-invasive or open. For example, the surgical stapler 2 may be used to staple wounds or incisions in the skin together, for cardiac surgery, for hernia repair, for abdominal wall closure, for anti-reflux or other bariatric procedures, for intestinal repair, for dura mater surgery or other brain surgery, for aneurysm closure, for anastomosis, or for any other suitable medical use.

Figure 8:
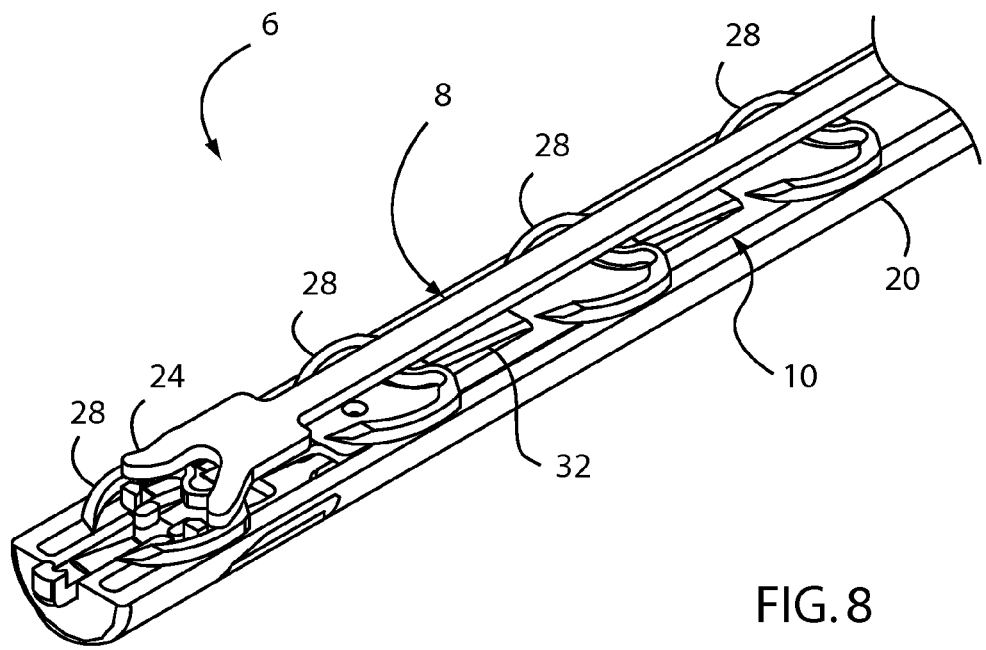
FIG. 8 is a cutaway perspective view of an exemplary effector of the surgical stapler of FIG. 1, where the effector is in an initial configuration.

The distal end of the effector 6 may be placed in proximity to the tissue to be stapled. For clarity in describing the operation of the stapler 2, that tissue is not shown in the figures. Referring to FIGS. 2 and 8, at this time the effector 6 may be in an initial state. The user then actuates the handle 4 and/or other component of the surgical stapler 2 to begin the deployment sequence. As described above, the handle 4 or other mechanism controls the motion of the components of the effector 6 in any suitable manner. First, the pusher 10 is advanced distally, while the splay arm 12 is maintained in substantially the same location. Thus, the pusher 10 advances relative to the splay arm 12. The splay arm 12 is cammed downward from the pusher 10 as a result of contact between the camming bump 36 and the splay arm 12. The camming bump 36 may be in contact with the bar 52 of the splay arm 12 or with a different part of the splay arm 12. As a result, at least the distal end of the splay arm 12 is held at a position spaced apart from the pusher 10. Alternately, the splay arm 12 is held at a position where at least part of it is spaced apart from the pusher 10 by a structure or mechanism other than or in addition to the camming bump 36. Alternately, the distal end of the splay arm 12 may be in contact with the pusher 10.

Next, as the pusher 10 continues to advance relative to the splay arm 12, the camming bump 36 slides into the aperture 54 of the splay arm 12. As a result, the camming bump 36 no longer pushes the splay arm 12 away from the pusher 10, or away from the pusher 10 to as great a degree. Advantageously, the distal end of the splay arm 12 is biased toward the pusher 10, such that the distal end of the splay arm 12 moves upward toward the pusher 10 after the camming bump 36 moves into the aperture 54. Such biasing may be accomplished in any suitable manner. Referring also to FIG. 8, as the distal end of the splay arm 12 moves upward toward the pusher 10, each splay tip 60 of a splay finger 58 moves upward to a location distal to a staple 28, such that each splay tip 60 is in the path of travel of the staple 28. Previously, each splay tip 60 had been positioned below, and out of the way of, the staples 28. Alternately, the splay arm 12 is not biased toward the pusher 10, and the splay fingers 58 are moved upward toward the pusher 10 in any other suitable manner.

In the initial configuration of the stapler 2, the distalmost staple 28 may be held by the notch 40 in the anvil 14. Before deployment of the first staple 28 by the stapler 2, it is possible that the distalmost staple 28 is not held by the notch 40 in the anvil 14. Instead, the notch 40 may be empty, and the distalmost staple 28 may be advanced into the notch 40 in the manner described below, after which point the stapler 2 is in the initial configuration.

Figure 10:
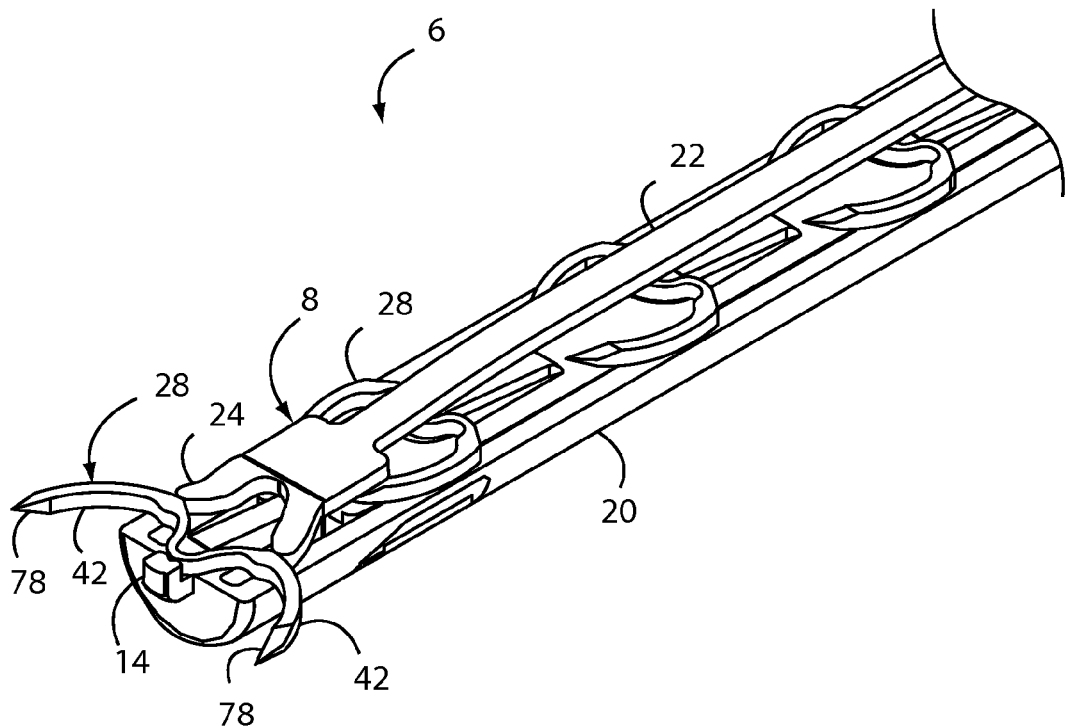
FIG. 10 is a cutaway perspective view of an exemplary effector of the surgical stapler of FIG. 1, where the effector is in a second configuration.

Next, referring also to FIG. 10, as the pusher 10 continues to advance relative to the splay arm 12, the camming bump 36 advances within the aperture 54 of the splay arm 12. As the pusher 10 advances relative to the splay arm 12, the anvil 14 may move distally as well, carrying the staple 28 held in the notch 40 distally as well. As the pusher 10 moves distally, it urges each valley 48 of the staple 28 against the corresponding splay tip 60 of the splay arm 12. Each splay tip 60 is positioned sufficiently far from the longitudinal centerline of the staple 28 that a moment is generated about that splay tip 60 by the advancement of the trough 46 of the staple 28 by motion of the anvil 14 substantially along the longitudinal centerline of the pusher 10. This moment causes the corresponding tine 42 of the staple 28 to move outward from the longitudinal centerline of the staple 28. Each splay tip 60 may be shaped, sized, positioned or otherwise configured in any manner that results in such a moment and the resultant motion of the tines 42 of the staple 28. The splay arm 12 is biased proximally, thus providing an opposing force on the splay tips 60, such that the staple 28 has a force to deform against. Indeed, by selecting a particular biasing force that is exerted proximally on the splay arm 12, the staples 28 are consistently deformed by a constant and known force.

Thus, as the pusher 10 exerts a distal force on the staple 28, the distal ends of the tines 42 of the staple 28 move apart from one another, each in a direction away from the longitudinal centerline of the staple 28. This deformation of the staple may be referred to as "splaying." During splaying of the staple 28, the tines 42 themselves may remain substantially undeformed; rather, a portion of the staple 28 in proximity to each peak 44 and/or the trough 46 may deform. Alternately, at least one tine 42 may deform during splaying of the staple 28. Further, referring also to FIG. 9, as the distal ends of the tines 42 move away from the longitudinal centerline of the staple 28, at least part of each tine 42 may move outward from the case halves 18, 20 through a slot 19 in the case halves 18, 20 or the like. As a result, the tines 42 of the staple 28 may move apart from one another a distance greater than the diameter of the housing formed by the case halves 18,20. Thus, splaying allows the staple 28 to grasp a greater amount of tissue than a conventional staple that does not splay, which is particularly useful in minimally-invasive surgery where the diameter of the housing is small. Alternately, where the stapler 2 is not used for minimally-invasive surgery, at least one staple 28 may extend out of the slot 19 in the initial configuration prior to splaying. Where the staple 28 is made from a plastically-deformable material such as stainless steel, the staple 28 deforms plastically as it splays from its initial configuration to the splayed configuration. Alternately, the staple may be elastically-deformable from its initial configuration to the splayed configuration. The staple 28 may be spring-loaded inwards to the initial configuration, such that the staple 28 springs outward and returns to the splayed configuration upon application of force such that the staple 28 is free to spring outward. Alternately, the staple 28 does not deform or move to a splayed configuration at all; rather, it may transition directly from the initial configuration to a closed configuration as described below.

If the distal end of the effector 6 has not yet been placed in the desired position, the motion of the pusher 10 may be stopped at this point, such that the user can place the distal end of the effector 6 that carries the splayed staple 28 in a desired location on the patient's anatomy. In this way, the user may obtain greater control over the stapling procedure and ensure that the splayed staple 28 is in the correct position before continuing actuation of the stapler 2 to close the staple 28 onto tissue.

Next, as the pusher 10 continues to advance relative to the splay arm 12, the camming bump 36 slides into contact with the distal end of the aperture 54 of the splay arm 12. The camming bump 36 and the distal end of the aperture 54 are both shaped and sized such that the camming bump 36 engages the distal end of the aperture 54 and consequently pushes the splay arm 12 distally. After the camming bump 36 engages the distal end of the aperture 54, the pusher 10 and splay arm 12 advance substantially together. As the pusher 10 moves distally, it continues to advance the staple 28 (held by the notch 40 in the anvil 14) distally as well.

Next, the pusher 10 continues to advance distally, continuing to push the splay arm 12 distally with it. Referring also to FIG. 7, as the splay arm 12 moves distally, at least one ear 56 of the splay arm 12 moves into contact with a corresponding ramp 74 defined in the lower case half 20. Alternately, the ramp 74 may be defined also, or instead, in the upper case half 18. As described above, the ramp 74 is oriented in a direction that is angled or curved downward in the distal direction. Advantageously, two ramps 74 are defined in the lower case half 20, one ramp 74 corresponding to each ear 56 of the splay arm 12. As the splay arm 12 moves distally, engagement between at least one ear 56 of the splay arm 12 and the corresponding ramp 74 causes the distal end of the splay arm 12 to move downward relative to the pusher 10. As the distal end of the splay arm 12 moves downward, each splay tip 60 of a splay finger 58 moves downward relative to the splayed staple 28, out of the way of the tines 42. In this way, the splay tips 60 do not interfere with closure of the staple 28. Optionally, the pusher 10 may continued to advance distally after the staple 28 has been splayed. The motion of the staple 28 between its splaying and the entry of the tines 42 into tissue may be referred to as "shuttling." During shuttling, the compressive force that deformed the staple 28 into the splayed configuration is substantially removed from the staple 28, and the staple 28 is substantially free to move distally. If the staple 28 has not been placed into contact with the tissue to be stapled by this time, the user now does so.

Next, the motion of the pusher 10 substantially stops, and the driver 8 advances distally relative to the pusher 10. Alternately, the motion of the pusher 10 distally slows, or the pusher 10 begins translation proximally, as the driver 8 advances distally relative to the pusher 10. Before the driver 8 begins to advance distally relative to the pusher 10, the driver 8 may have been stationary, or may have been moving distally at the same speed or at a slower speed than the pusher 10. As the driver 8 advances, at least one of the prongs 24 and/or crossbar 26 moves into contact with a corresponding ramp 76 defined in the upper case half 18. Alternately, a different part of the driver 8 contacts the ramp 76. At least the distal end of the driver 8 is biased upward relative to the pusher 10, such that the driver 8 encounters the ramp 76. As described above, the ramp 76 is oriented in a direction that is angled or curved downward in the distal direction. As the driver 8 moves distally, engagement between at least one of the prongs 24 and/or crossbar 26 of the driver 8 and the ramp 76 causes the distal end of the driver 8 to move downward relative to the pusher 10. Thus, the prongs 24 are moved downward to a position proximal to and in line with the splayed staple 28. The ramp 76 and/or the upper case half 18 are shaped to allow the prongs 24 to move substantially distally and substantially linearly after the prongs 24 have moved to a position proximal to and in line with the splayed staple 28.

Figure 11:
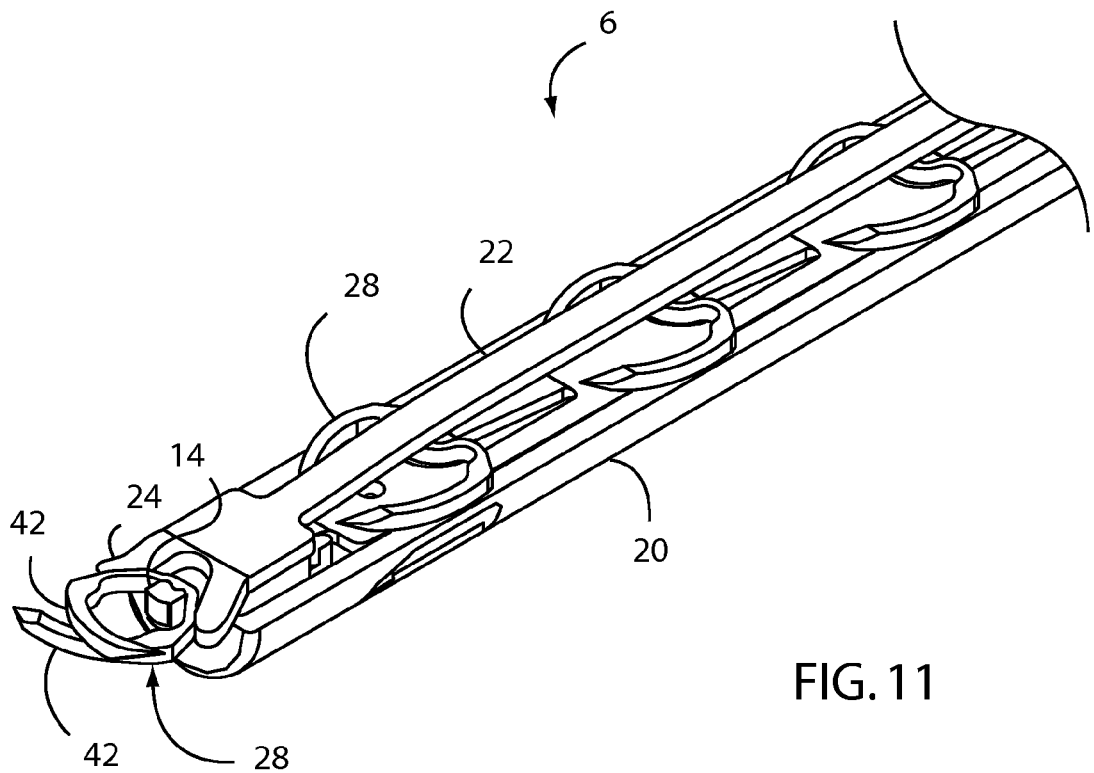
FIG. 11 is a cutaway perspective view of an exemplary effector of the surgical stapler of FIG. 1, where the effector is in a third configuration.

Referring also to FIG. 11, the driver 8 continues to move distally, each prong 24 contacts a corresponding peak 44 of the staple 28. Each peak 44 of the staple 28 is offset from the longitudinal centerline of the staple 28. Further, the longitudinal centerline of the staple 28 substantially intersects or approaches close to intersection with the notch 40 in the anvil 14, which holds the trough 46 of the staple 28. As a result, each peak 44 of the staple 28 is offset from the notch 40. The force exerted by each prong 24 distally on the corresponding peak 44 of the staple 28, which is offset from the longitudinal centerline of the staple 28, results in at least one moment exerted on the staple 28 about the notch 40. That is, because the notch 40 holds the trough 46 of the staple 28 and substantially prevents the staple 28 from moving, the force exerted distally by the driver 8 via the prongs 24, the distal force exerted by each prong 24 is transformed into a moment about the notch 40. Each tine 42 of the staple 28 that experiences that moment moves toward the longitudinal centerline of the staple 28. In the course of this motion, the distal ends of the tines 42 may first move toward the longitudinal centerline of the staple 28 and toward one another, cross each other, then move away from the longitudinal centerline of the staple 28 and away from one another. The tines 42 need not substantially change shape as they move; rather, they may rotate about a pivot point located at or near the trough 46. Alternately, one or both of the tines 42 may deform as they move. The radius of curvature of each tine 42 may be substantially coincident with its path of travel during closure of the staple 28.

As the driver 8 continues to move distally, the staple 28 continues to deform against the portion of the anvil 14 distal to the notch 40. This deformation may be plastic deformation from the splayed configuration to a final, closed configuration. Alternately, this deformation may be elastic. Alternately, one of the splaying and the closing of the staple 28 may deform the staple 28 plastically, with the other being performed elastically. The staple 28, prongs 24 and/or any other component of the effector 6 may be shaped or otherwise configured such that the tines 42 swipe past one another as the staple 28 moves to the closed configuration. As one example, the distal end of each tine 42 may include an angled or curved surface 78 that is oriented in substantially the opposite direction as that of the other tine 42. That is, the distal end of one tine 42 may include a lower surface 78 near its distal end that is angled upward in the distal direction, and the distal end of the other tine 42 may include an upper surface 78 near its distal end angled downward in the distal direction. Contact between the surfaces 78 of the tines 42 thus causes the tines 42 to slide past each other, with one tine 42 moving upward and/or the other tine 42 moving downward, such that the tines 42 swipe past one another and are out of plane relative to one another. As another example, the distal end of each tine 42 may be shaped substantially conically, such that contact between the distal ends of the tines results in the tines 42 swiping past one another in a similar manner. As another example, the staple 28 may be shaped in any other manner such that the application of force longitudinally thereto causes the tines 42 to move in a direction that has a component of motion perpendicular to the longitudinal direction, thereby moving the tines 42 such that they swipe past each other. Alternately, at least two tines 42 of the staple 28 are configured to interfere with or otherwise engage one another when the staple 28 is in the closed position.

Referring also to FIG. 11, when deformation of the tines 42 of the staple 28 is complete, the staple 28 is in the closed configuration. In that closed configuration, at least part of each tine 42 of the staple 28 is located within tissue of the patient. The closed staple 28 may now slip out of the notch 40 as the effector 6 is moved by the user. That is, after the staple 28 is formed, the user moves the effector 6 in a direction away from the notch 40, such that the holding force exerted on tissue by the closed staple 28 holds the staple 28 in place and allows the staple 28 to slip out of the notch 40. This may be referred to as passively releasing the closed staple 28. Alternately, the effector 6 may be configured to actively release the staple 28 from the effector 6 after the staple 28 is closed, such as by ejecting the staple 28. If the user does not wish to deploy any other staples 28, or if no more staples 28 remain in the effector, then the operation of the surgical stapler 2 is complete.

Operation—Integrated Splay Arm and Anvil

In another example of an effector 6, the anvil and splay arm may be integrated. For clarity and brevity, only the significant differences between operation of this exemplary effector 6 and the effector 6 described earlier in this document are set forth here. Referring to FIG. 12, the effector 6 is in an initial state. The user then actuates the handle 4 and/or other component of the surgical stapler 2 to begin the deployment sequence. In the initial state, the staple 28 and the driver 8 do not extend laterally beyond the housing formed by the case halves 18, 20. Alternately, part of the staple 28 and/or driver 8 may extend laterally beyond the housing formed by the case halves 18, 20.

Figure 14:
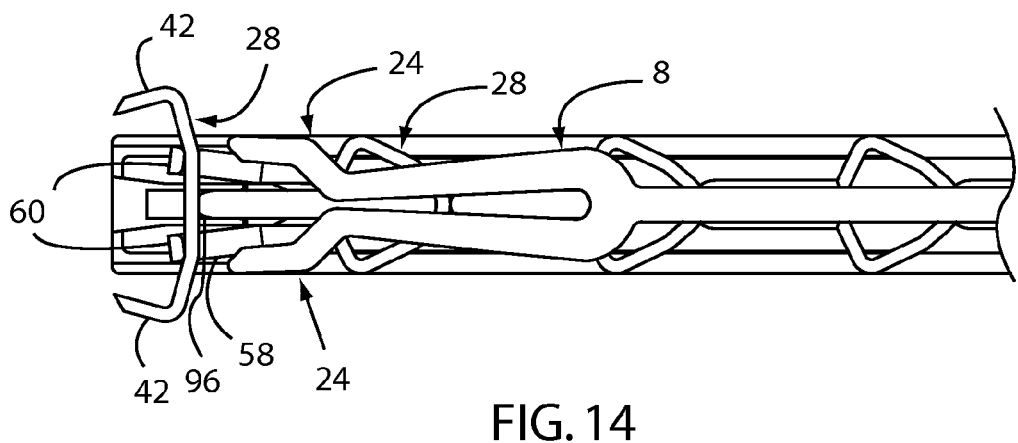
FIG. 14 is a top cutaway view of the exemplary effector of FIG. 12 in a second configuration.
Figure 15:
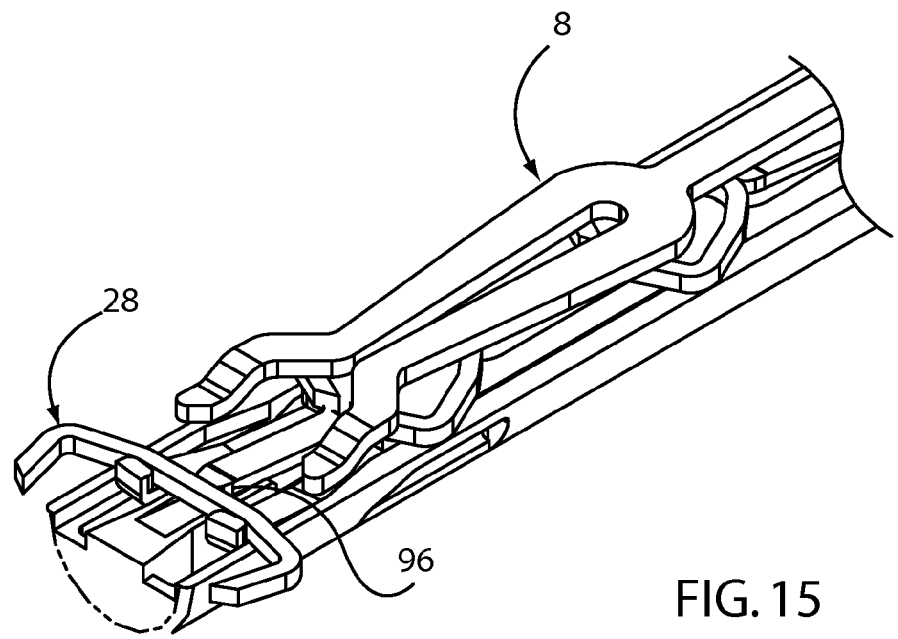
FIG. 15 is a perspective cutaway view of the exemplary effector of FIG. 12 in the second configuration of FIG. 14.

To splay the distalmost staple 28, both the splay arm 12 and the pusher 10 are advanced. The pusher 10 is advanced faster than the splay arm 12. The distal end 96 of the pusher 10 is sized and positioned to contact the apex 47 of the staple 28. The distal end 96 of the pusher 10 may be in contact with the apex 47 of the staple 28 when the effector 6 is in the initial state. Alternately, the distal end 96 of the pusher 10 may be spaced apart from the apex 47 of the staple 28 in the initial state, and then move into contact with the apex 47 of the staple 28. Alternately, the distal end 96 of the pusher 10 may contact a different part of the staple 28. As the pusher 10 advances distally, it pushes the staple 28 distally. The pusher 10 advances faster than the splay arm 12, and thus faster than the splay tips 60. As a result, as the pusher 10 moves distally, it exerts a distal force on the staple 28. Referring also to FIGS. 14-15, each splay tip 60 is positioned sufficiently far from the longitudinal centerline of the staple 28 that a moment is generated about that splay tip 60 by the force exerted substantially along the longitudinal centerline of the pusher 10 by the distal end 96 of the pusher 10. Advantageously, each splay tip 60 contacts a corresponding inflection point 49 of the staple. Further, as the splay arm 12 moves distally, contact between each splay finger 58 and the corresponding wedge surface 82 causes the splay fingers 58 to move apart. That is, contact between the splay fingers 58 and the wedge 80 as the splay arm 12 moves distally counteracts the inward bias of the splay fingers 58. As the splay fingers 58 move apart, each splay tip 60 continues to remain substantially in contact with the corresponding inflection point 49 of the staple 28. In this way, the staple 28 continues to splay about the inflection points 49 even as the inflection points 49 move laterally outward during splaying. The angle of the wedge surfaces 82 and the shape of the splay fingers 58 are selected to maintain each splay tip 60 substantially in contact with the corresponding inflection point 49 during splaying. The moment generated about each splay tip 60 causes the staple 28 to bend about each inflection point 49. As a result, the tines 42 of the staple 28 move outward from the longitudinal centerline of the staple 28. Splaying thus results from differential longitudinal motion of the pusher 10 and the splay arm 12.

As described above, the staple 28 deforms plastically as it splays from its initial configuration to the splayed configuration. Alternately, the staple may be elastically-deformable from its initial configuration to the splayed configuration. During splaying of the staple 28, the tines 42 themselves may remain substantially undeformed; rather, the spine 45 of the staple 28 may deform. Alternately, at least one tine 42 may deform during splaying of the staple 28. Referring also to FIGS. 14-15, in the splayed configuration, the tines 42 of the staple 28 are oriented generally distally. Such an orientation may facilitate penetration of tissue substantially perpendicularly. Alternately, the tines 42 may be oriented in any other suitable direction when the staple 28 is in the splayed configuration.

Figure 16:
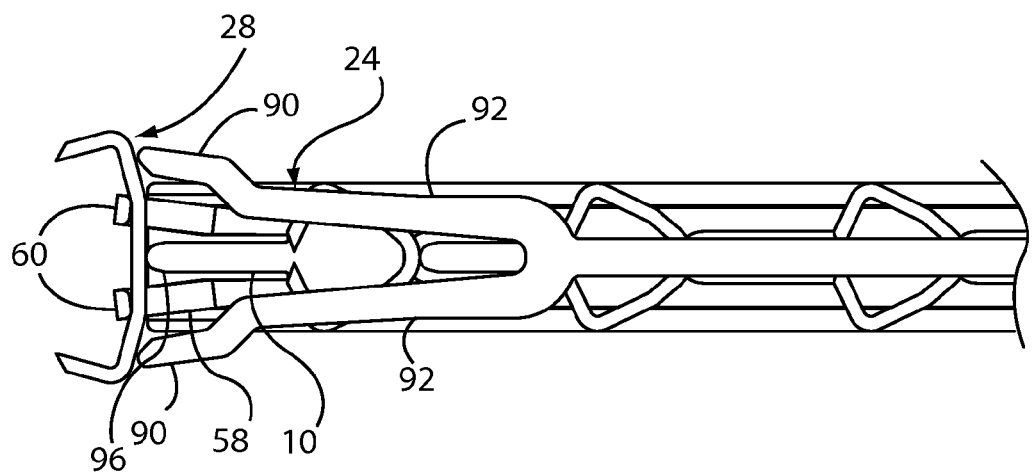
FIG. 16 is a top cutaway view of the exemplary effector of FIG. 12 in a third configuration.

Next, referring also to FIG. 16, the splayed staple 28 is advanced into tissue. Advancing the staple 28 may be performed in any suitable manner. As one example, the pusher 10 and the splay arm 12 are advanced distally at substantially the same rate. Alternately, the staple 28 is not substantially advanced after splaying, and the staple 28 is instead closed after splaying. As the staple 28 is advanced into tissue, the driver 8 advances distally. As the driver 8 advances distally, each distal arm 90 of each prong 24 moves outward through the slot 19 or other opening in the housing of the effector 6. Such motion results from the outward bias of the prongs 24; when each prong 24 encounters a slot 19, the distal arm 90 is free to move outward. Alternately, one or more prongs 24 are not biased outward, and instead are actively deflected outward through the slot 19 or other opening in the housing. Alternately, the driver 8 is not advanced distally until a later time.

Figure 17:
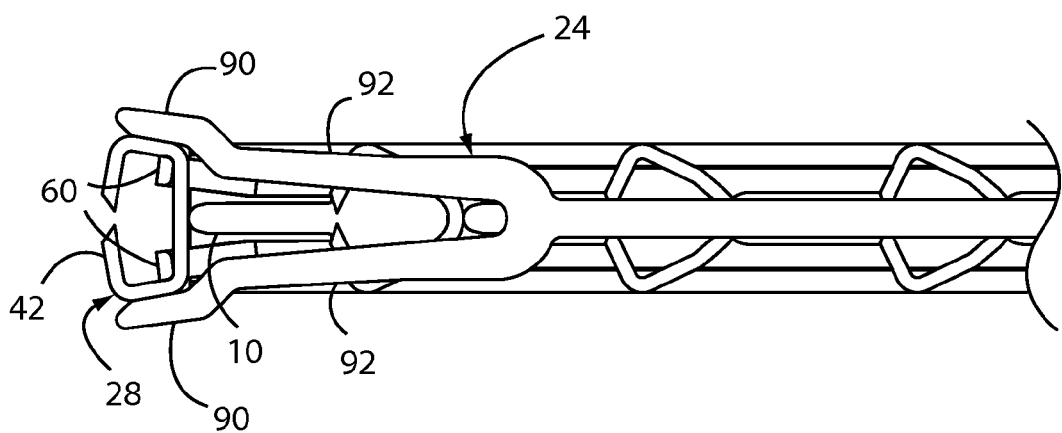
FIG. 17 is a top cutaway view of the exemplary effector of FIG. 12 in a fourth configuration.

Next, referring also to FIG. 17, the staple 28 is moved to a closed configuration. The closed configuration of the staple 28 may be different from both the initial and the splayed configurations. Closing the staple 28 may be performed in any suitable manner. As one example, the pusher 10 and the splay arm 12 are held in substantially the same position, and the driver 8 is advanced. As the driver 8 is advanced, the distal end of the distal arm 90 of each prong 24 contacts the staple 28 at a location laterally outward from the location at which the corresponding splay tip 60 contacts the staple 28. That is, the distal end of the distal arm 90 of each prong 24 contacts the staple 28 at a location laterally outward from the corresponding inflection point 49. The force exerted by each prong 24 distally on the staple 28, which is offset from the longitudinal centerline of the staple 28, results in at least one moment exerted on the staple 28 about the corresponding splay tip 60. The staple 28 deforms as a result of those moments. Such deformation is advantageously about the inflection points 49. In this way, the splay tips 60 act as anvils. As the driver 8 continues to move distally, the distal ends of the distal arms 90 of the prongs 24 have deformed the staple 28 to such a degree that they no longer contact the staple 28. Instead, the inner surface of each distal arm 90 contacts the staple 28 and may continue to deform the staple 28 to the closed configuration. During closing of the staple 28, the tines 42 themselves may remain substantially undeformed; rather, the spine 45 of the staple 28 may deform. Alternately, at least one tine 42 may deform during splaying of the staple 28.

Operation—Resetting Effector for Deployment of Next Staple

If the user wishes to deploy another staple 28, then the user continues to actuate the handle 2 in any suitable manner. The effector 6 is controlled such that its components return to their initial position. Alternately, the effector 6 does not return completely to its initial configuration. First, the driver 8 is moved proximally in any suitable manner. For example, the driver 8 may be biased proximally, such that the driver 8 may be released and simply return to its initial position as a result of a biasing force. Alternately, the driver 8 may be retracted actively in the proximal direction, instead or of in addition to the presence of a biasing force. The driver 8 may be biased upward relative to the pusher 10, such that as the driver 8 retracts proximally, the driver 8 moves upward, away from the pusher 10, and into contact with the ramp 76 in the upper case half 18. The path followed by the driver 8 as it retracts proximally may be substantially the same path followed by the driver 8 as it advanced distally, in reverse. However, if desired the driver 8 may retract proximally along a different path than the driver 8 followed during its distal advance. When the driver 8 returns to its initial position, with the prongs 24 above the pusher 10 and out of the path of travel of the staple or staples 28 held by the pusher 10, motion of the driver 8 may stop. The motion of the driver 8 back to its initial position may be performed before, during or after actuation of the other components of the effector 6 to reset the effector 6 for deployment of another staple 28. The order in which actuation of different components of the effector 6 is described here is merely exemplary, and does not limit the order of actuation of the components of the effector 6.

The pusher 10 is moved proximally in any suitable manner. For example, the pusher 10 may be biased proximally, such that the pusher 10 may be released and simply return to its initial position as a result of a biasing force. Alternately, the pusher 10 may be retracted actively in the proximal direction, instead or of in addition to the presence of a biasing force. The path followed by the pusher 10 as it retracts proximally may be substantially the same path followed by the pusher 10 as it advanced distally, in reverse. However, if desired the pusher 10 may retract proximally along a different path than the pusher 10 followed during its distal advance.

As the pusher 10 retracts, friction between the pusher 10 and each remaining staple 28 results in a proximal force exerted on each staple 28. The anti-backup rack 16 counteracts that force and prevents the staples 28 from being dragged proximally along with the pusher 10. As described above, tines 64 may extend from the spine 62 of the anti-backup rack 16, and the distal end of each tine 64 may be positioned substantially proximal to a corresponding staple 28. Advantageously, the tines 64 are paired, and each tine 64 of a pair contacts a different peak 44 of the staple 28. Contact between each tine 64 and the corresponding staple 28 counteracts the proximal force exerted on each staple 28 by friction, thereby holding each staple 28 at substantially the same longitudinal position in the effector 6 as the pusher 10 is retracted. Alternately, the anti-backup rack 16 restrains each staple 28 against proximal motion in a different manner. Alternately, the anti-backup rack 16 is not used, and the effector 6 restrains each staple 28 against proximal motion in a different manner.

As the pusher 10 continues to move proximally, at least one of the tabs 32 extending upward from the pusher 10 slides underneath a staple 28 previously located proximal to it. That staple 28 is held in place by at least one of the tines 64 of the anti-backup rack 16. Because the staple 28 is held in place and does not substantially move proximally, up or down, the tab 32 bends downward as it slides underneath the staple 28. After the distal end of the tab 32 has been pulled out from underneath the staple 28, the tab 32 once again moves back up to its previous configuration, because the distal end of the tab 32 is biased upward. Thus, the distal end of the tab 32 is then located proximal to and substantially in line with the staple 28. Advantageously, the tab 32 is located proximal to and in line with the trough 46 of the staple 28.

The splay arm 12 is moved proximally in any suitable manner, in conjunction with or independently of the motion of the pusher 10. The path followed by the splay arm 12 as it retracts proximally may be substantially the same path followed by the splay arm 12 as it advanced distally, in reverse. However, if desired the splay arm 12 may retract proximally along a different path than the splay arm 12 followed during its distal advance. The splay arm 12 may be biased proximally by the coil spring 70 or other mechanism or structure, as described above. As the pusher 10 moves proximally, the camming bump 36 of the pusher 10 continues to engage the distal end of the aperture 54 in the splay arm 12. As the pusher 10 continues to move proximally, the splay arm 12 moves proximally with it. The splay arm 12 then reaches a position at which there is no further tension in the coil spring 70, and the splay arm 12 ceases its proximal motion. The projection 72 or other part of the splay arm 12 may encounter a hard stop at this time as well, where the hard stop prevents further proximal motion of the splay arm 12. The hard stop may be a feature defined in the lower case half 20, may be a different component of the effector 6, or may be omitted. After the splay arm 12 ceases its proximal motion, the pusher 10 continues to move proximally. The camming bump 36 moves proximally along the aperture 54, then up and out of the aperture 54 to a location proximal to the aperture 54, pushing the splay arm 12 downward from the pusher 10. The effector 6 is now once again in its initial configuration, and the next staple 28 may be deployed in the same manner as described above.

While the invention has been described in detail, it will be apparent to one skilled in the art that various changes and modifications can be made and equivalents employed, without departing from the present invention. It is to be understood that the invention is not limited to the details of construction, the arrangements of components and/or the details of operation set forth in the above description or illustrated in the drawings. Headings and subheadings are for the convenience of the reader only. They should not and cannot be construed to have any substantive significance, meaning or interpretation, and should not and cannot be deemed to be limiting in any way, or indicate that all of the information relating to any particular topic is to be found under or limited to any particular heading or subheading. The contents of each section of this document are merely exemplary and do not limit the scope of the invention or the interpretation of the claims. Therefore, the invention is not to be restricted or limited except in accordance with the following claims and their legal equivalents.

What is claimed is:

1. A method for surgically stapling tissue, comprising:
    providing a surgical stapler comprising
        at least one staple,
        a pusher configured to hold said at least one staple,
        a splay arm movable relative to said pusher, said splay arm including two spaced-apart splay tips, and
        a driver movable relative to said pusher;
    splaying at least one said staple by plastically deforming the distalmost said staple against said splay tips; and
    after said splaying, closing at least one said staple by plastically deforming the distalmost said staple against said splay tips.

2. The method of claim 1, incorporating by reference all of the elements of that claim; further comprising advancing said staple distally after said splaying and before said closing.

3. The method of claim 1, incorporating by reference all of the elements of that claim; wherein said staple has at least two tines each having a free end, and wherein said splaying orients said free ends of said tines generally distally.

4. The method of claim 1, incorporating by reference all of the elements of that claim; wherein said splaying is performed by moving at least one of said splay arm and said pusher relative to the another.

5. The method of claim 1, incorporating by reference all of the elements of that claim; wherein each said staple includes at least two inflection points therein; wherein said splay tips move laterally outward during said splaying to contact and remain in contact with said inflection points.

6. The method of claim 1, incorporating by reference all of the elements of that claim; wherein the driver comprises at least two spaced-apart prongs; and wherein said closing comprises first contacting the distalmost said staple with the distal ends of said prongs, then contacting the distalmost said staple with an inner surface of each said prong.

7. The method of claim 1, incorporating by reference all of the elements of that claim; further comprising passively releasing the distalmost said staple after said closing.

8. The method of claim 1, incorporating by reference all of the elements of that claim; wherein said surgical stapler includes a plurality of said staples; further comprising, after said closing, advancing the remainder of said staples distally, then repeating said splaying and said closing.

9. A method for surgically stapling tissue, comprising:
    providing a surgical stapler comprising
        a plurality of staples,
        a pusher configured to hold said staples,
        a splay arm movable relative to said pusher, a driver movable relative to said pusher,
  wherein said pusher, said splay arm and said driver are initially in a first configuration relative to one another;
splaying at least one said staple to a splayed state;
after said splaying, closing at least one said splayed staple, after which said pusher, said splay arm and said driver are in a second configuration relative to one another; and
resetting said stapler to said first configuration of said pusher, said splay arm and said driver;
wherein said splaying and said closing each plastically deform at least one said staple.

10. The method of claim 9, incorporating by reference all of the elements of that claim; further comprising repeating splaying and closing after said resetting.

11. The method of claim 9, incorporating by reference all of the elements of that claim; wherein said splaying is performed by advancing said splay arm and said pusher distally, wherein said pusher is advanced faster than said splay arm.

12. The method of claim 11, incorporating by reference all of the elements of that claim; wherein said resetting includes retracting said pusher and said splay arm proximally.

13. The method of claim 12, incorporating by reference all of the elements of that claim; wherein said surgical stapler includes an anti-backup rack substantially fixed relative to said pusher and said driver; further comprising holding at least one staple substantially stationary with said anti-backup rack during said retracting said pusher.

14. The method of claim 13, incorporating by reference all of the elements of that claim; wherein said resetting includes retracting said driver proximally.

15. The method of claim 9, incorporating by reference all of the elements of that claim; wherein said closing is performed by holding said splay arm and said pusher substantially stationary and advancing said driver distally.

16. The method of claim 9, incorporating by reference all of the elements of that claim; wherein said splay arm further comprises two spaced-apart splay tips; and wherein said splaying comprises plastically deforming the distalmost said staple against said splay tips.

17. The method of claim 9, incorporating by reference all of the elements of that claim; wherein said splay arm further comprises two spaced-apart splay tips; and wherein said closing comprises plastically deforming the distalmost said staple against said splay tips.

* * * * *